United States Patent [19]
Tichy

[11] Patent Number: 6,029,769
[45] Date of Patent: Feb. 29, 2000

[54] PERMEABLE AERODAM TO REDUCE WIND NOISE

[76] Inventor: James B. Tichy, P.O. Box 1308, Sausalito, Calif. 94966

[21] Appl. No.: 08/896,565

[22] Filed: Jul. 18, 1997

[51] Int. Cl.[7] .................................................. H04R 25/00
[52] U.S. Cl. ................................. 181/136; 2/209; 2/423
[58] Field of Search .................................... 181/129, 133, 181/136; 2/209, 423

[56] References Cited

U.S. PATENT DOCUMENTS

| | | | |
|---|---|---|---|
| 4,370,758 | 2/1983 | Mattheis | 2/423 |
| 5,086,789 | 2/1992 | Tichy | 2/209 |
| 5,477,564 | 12/1995 | Tichy | 2/209 |

*Primary Examiner*—Khanh Dang

[57] ABSTRACT

A permeable aerodam 10 is fastened to a front helmet strap 16 of a bicycle rider's helmet 18. The aerodam includes a shaped fiber filter 32 which is mounted on a base 36 and is designed to impede, but not arrest the motion of air flowing through it. The aerodam also includes a matrix 52 which includes the base and which shapes, supports, and locates the filter next to the temple area. A headwind experienced by the rider flows around the side of the head and partially through the aerodam such that an impedance gradient caused by the shaped filter will cause a quiet retrolaminar flow velocity profile 92 alonside the rider's ear canal. The effect eliminates the onset of noisy turbulence heard by the rider while allowing unobstructed ambient sounds and ventilation to be enjoyed.

18 Claims, 6 Drawing Sheets

PERMEABLE AERODAM TO REDUCE WIND NOISE

BACKGROUND—FIELD OF THE INVENTION

This invention relates to the class of apparel or prosthetics used to abate the sound of wind turbulence experienced by bicyclists, motorcyclists, sailors and equestrians when facing into a headwind.

BACKGROUND—DESCRIPTION OF THE PROBLEM

Turbulence is created alongside the head because the air flow cannot remain attached past the high curvature of the cheekbone area. Instead, it separates in a turbid flow pattern resulting in a noise spectrum which varies among individual facial features as well as the relative wind speed, air density and humidity (U. R. Kristiansen, et. al.).

I tried to imagine the character of this sound while bicycling into a headwind. At a relative 20 miles per hour at sea level, the flow noise sounded like a pair of flexible aluminum sheets vibrating softly and rapidly very close by. As the wind speed increased to 30 mph, the imaginary metal sheets hardened to a sharper sounding sheet steel and vibrated with more violent motion. The higher the speed, the higher the frequency bands and the louder the noise. Indeed, the spectral power density increases as the cube of the speed.

For motorcyclists, the sound is more deafening. It is alarming that up to 46% of all motorcyclists wearing half helmets, or no helmets at all, suffer some hearing loss due to turbulent wind noise around the helmet (Smith). The hearing loss is not caused by engine noise. The brain may "turn off" to the flow noise, but for some, permanent loss of hearing is inescapable.

For bicyclists, the effects are not as severe, but can still be distracting, and under certain conditions can confuse or muddy important ambient sounds, such as the tire noise of a vehicle approaching from the rear. In this case vehicles must get much closer to the rider before the awareness threshold is met, (W. K. Van Moorheim, et.al.).

BACKGROUND—PRIOR ART

The current state of the art of flow noise abatement relies on deflection of the flow. To work well the deflector must be located directly over the ear. One overriding disadvantage is that the greater the flow noise abatement, the larger the deflector must be, rendering an overprotected look. Ventilation also suffers.

Two examples illustrate the difficulty in abating the noise with the deflector method. The first is illustrated in my own U.S. Pat. No. 5,477,564 (1995) which cites covering the entire ear with a design having the upper and rear edges open for ventilation. In order to work properly, the earfoil must be adjusted away from the head to keep from touching and tickling the ear flange. The resulting size is then too large for warm weather marketing purposes.

The second example is illustrated in a pair of Wind Silencers which I purchased from the New York Design Studios. Although smaller and less noticeable than my earfoil design, the forward mounted deflectors with their hard trailing edges transform the turbulent noise into higher frequency bands, which effectively block out conversation and even more tire noise mentioned earlier.

BACKGROUND—THE AERODAM

The marriage of style and aerophysics forces a new tack. Instead of deflecting the boundary layer and letting the natural air flow determine the resulting velocity profile, perhaps one should create an artificial boundary layer which can be shaped at will by using a "soft" approach. For instance, birds have evolved a very sophisticated boundary layer control by the use of down feathers microscopically ribbed for viscosity control. Also, the aircraft industry has done much work in passive boundary layer control to prevent flow separation from occurring, usually with the idea that higher lift coefficients can be achieved. Methods vary from boundary layer fences mounted perpendicularly to the wing surface to microscopic roughened surfaces embedded or placed strategically in an existing surface at very low Reynolds numbers. For the reduction of pre existing turbulence, ceramic screens have been placed parallel to the turbulent flow such as in the nozzle wake of jet engines, or thin wire screens are placed perpendicularly to the flow as in wind tunnels for the standardization of inter aerodynamic data. Although all these systems are widely known, they require surface areas which are inappropriate for use on the human face and head.

In order to satisfy the marketing constraints of smallness or innocuousness, and yet affect a successful flow noise abatement device, I suggest an open sided filter which is mounted perpendicularly to the surface of the rider's head so that boundary layer stabilization is achieved at two zones: one in front of the aerodam, and the second behind the aerodam in the wake around the ear canal. The forward zone tends to remain laminar up to the filter because the flow has been pressurized around the convexity of the cheekbone. The rear zone relies on a filter which mimics, in-situ, all those factors that contribute to turbulent decay, namely a diffusion and damping process.

A DESCRIPTION OF DRAWINGS

FIGS. 3a through 3g are all left side sectional views.

DESCRIPTION OF EMBODIMENTS

Figure 1:
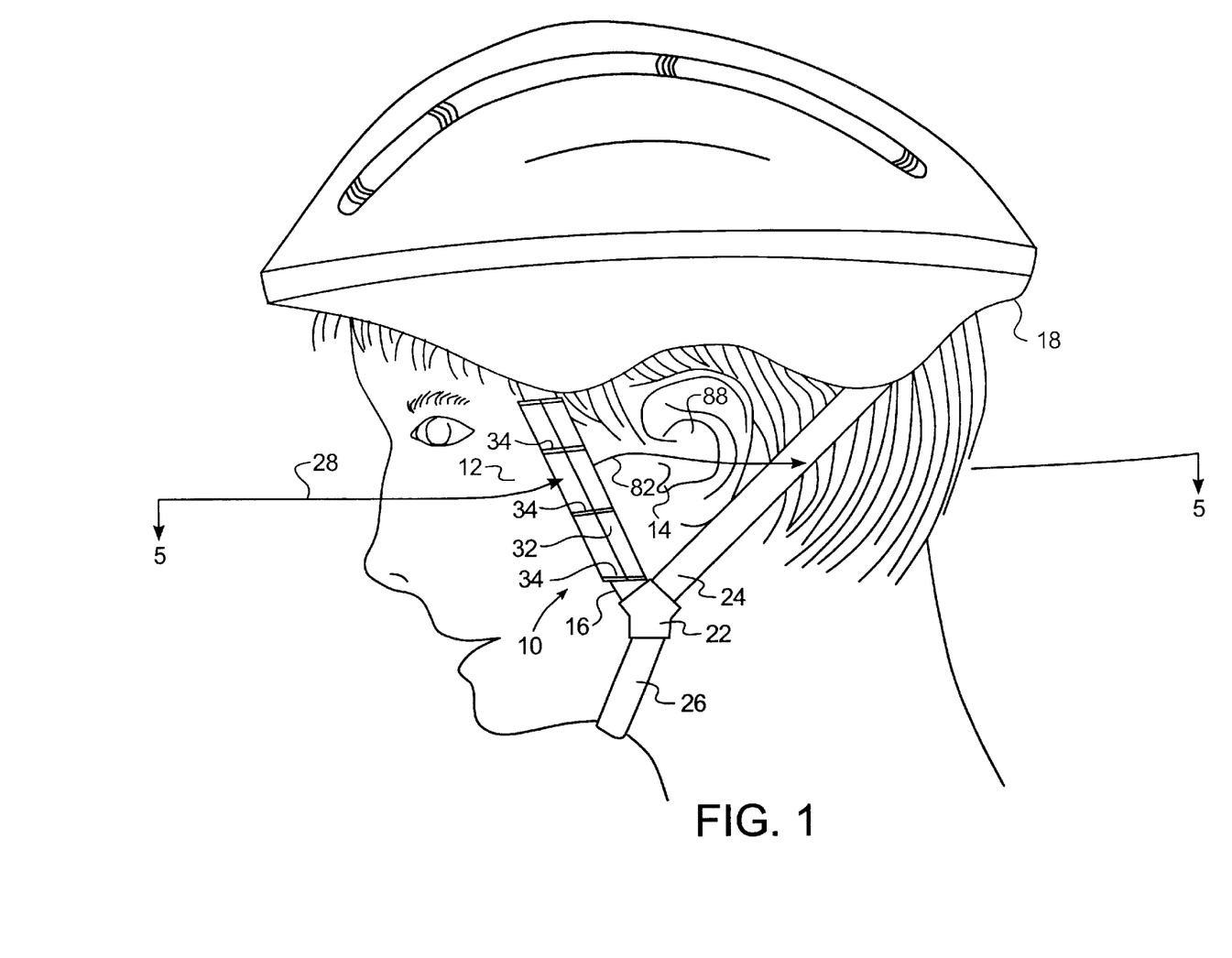
FIG. 1 shows the permeable aerodam fastened to the front helmet strap of helmet.
Figure 2:
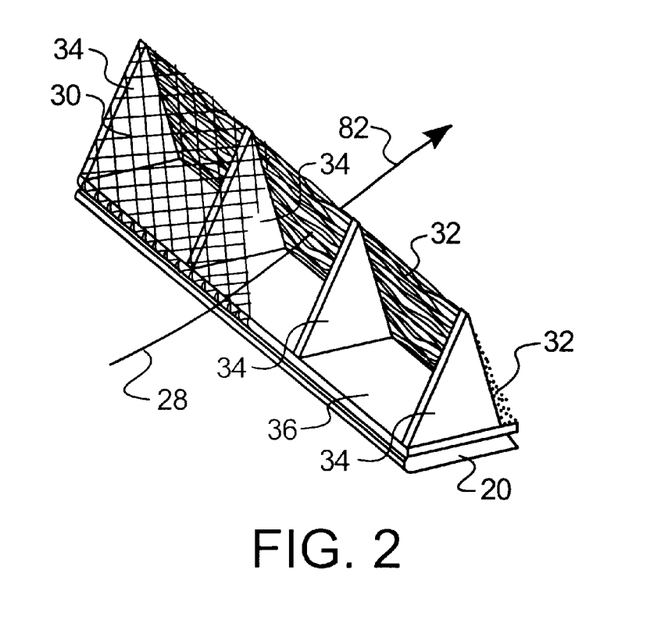
FIG. 2 shows the containment netting cut away to expose the abutments and their positions on the base as they position the anisotropic fiber filter in place.

Refer to FIG. 1. The permeable aerodam (dam) 10 is utilized to prevent turbulence along the side of the rider's head by placing it behind the cheekbone-eyebone area 12 and in front of the ear canal 14. The dam is conveniently fitted onto a front strap 16 of bicycle helmet 18 by a friction clip 20 which is glued to the bottom surface of base 36 as shown in FIG. 2. The front strap 16 is held in place by a strap buckle 22 which also connects a rear helmet strap 24 and lower chin strap 26.

In FIGS. 1 and 2 a headwind 28 approaches the side of the rider's head. The air flow closest to the head passes through the dam by first passing through a containment screen or netting 30 and then by tortuous path through a fiber filter or labyrinth 32.

Figure 3A:
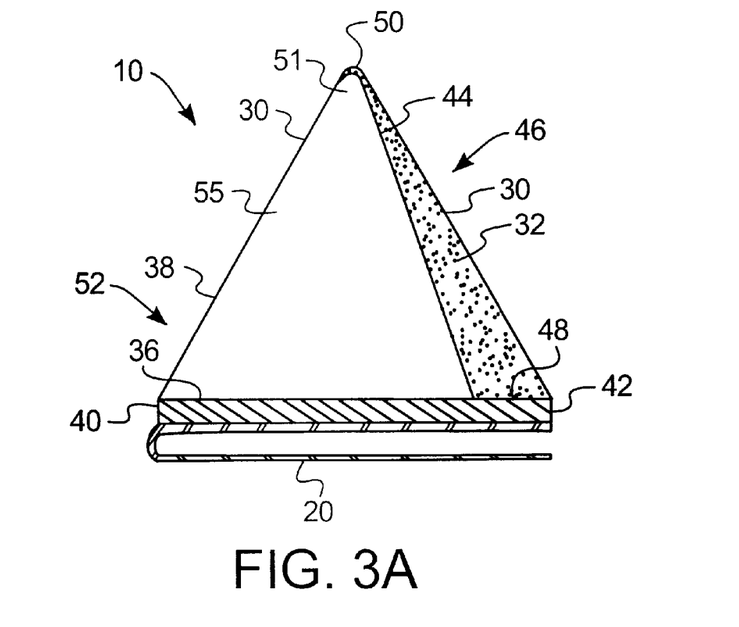
FIG. 3a is a sectional just in front of one of the abutments showing the anisotropic fibers, the surface of the abutment, the containment, base and strap clip.

Refer to FIGS. 2 and 3a. The filter 32 is held in position by a matrix 52 comprising a containment 30, a series of triangular foam abutments 34, and a base 36. The abutments, which are 2 milimeters thick are glued to the upper surface of the base 36 which is 3 mm thick. The containment is a netting woven with a 0.05 mm polyester monofilament thread thus forming a very light weight highly permeable tulle. The netting 30 covers the part of the dam above the base and is glued to the front edge 38 of all abutments as well as to the front edge 40 and rear edge 42 of the base. The front surface of the filter 32 is lightly glued to the rear edge 44 of abutment 34 and the rear surface 46 of filter 32 is lightly glued to the containment 30. The bottom 48 of the filter is glued to the top of the base 36 and the edge tip 50 or upper edge of filter 32 terminates at the tip 51 of the abutment 34. Thus, the filter is held firmly in position against wind pressure and rough handling.

The most effective, readily available and inexpensive flow impedance material which I have found is a polyester batting comprised of monofilaments 0.0125 mm to 0.025 mm in diameter and about 2.5 cm long each, and which are collectively woven and layered randomly into a fiber mass. Hundreds of fibers per cubic centimeter are loosely intermixed together resulting in a fiber density of 2% to 7%. Thus, there is a considerable amount of void volume for the air to flow through. The commercial name of the combed fiber is trademarked Mountain Mist Glazene, type 203 and is manufactured by the Stearns Technical Textile Company (STTC), Cincinnatti, Ohio, 45215. The type 203 is anisotropic in character, that is the fibers are combed so that a majority of them are caused to lay in one direction. There are uses for the uncombed isotropic type as well, such as type 605 which will be discussed in the variations.

FIG. 2 shows the anisotropic character of a type 203 fiber filter 32. The fibers are generally oriented so that they span the distance between adjacent abutments. This is done to increase the fabrication strength and to decrease the migration of the individual fibers. Although the fibers mentioned above are very useful and appropriate for cycle apparel, other fibers such as cotton, stainless steel wool, etc can be used to achieve the same result as will be discussed in the operation section.

Variations

Figure 3B:
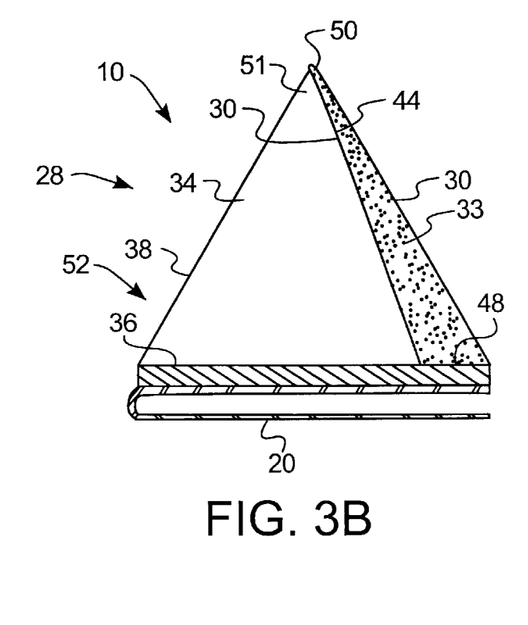
FIG. 3b shows the containment wrapped only around the filter.

Refer to FIG. 3b. The fiber filter does not require anisotropic or combed fiber direction provided the containment 30 is in contact with the filter on all sides. The isotropic filter such as type 605 can be used as an alternative. The containment is glued to edge 44 of abutment 34 and the bottom of the filter 33 is glued to the upper surface of base 36.

Figure 3C:
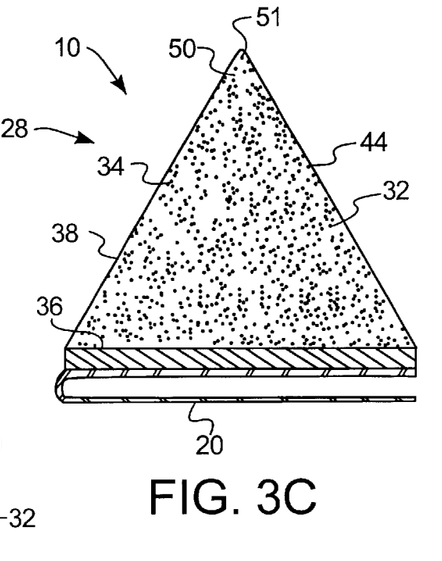
FIG. 3c shows the anisotropic fiber ends glued directly to the abutment surface. There is no containment.

Refer to FIG. 3c. There is no containment in this variation. Anisotropic fiber is glued to base 36 and the ends of the fibers are butt glued to the abutment surface 55. The outer extensions of the fibers are trimmed to the dimensional limits of the edges 38 and 44 of abutments 34. The lengths of the fibers are exposed to handling, but the elimination of the containment 30 decreases the flow impedance through the dam for quietest operation.

Figure 3D:
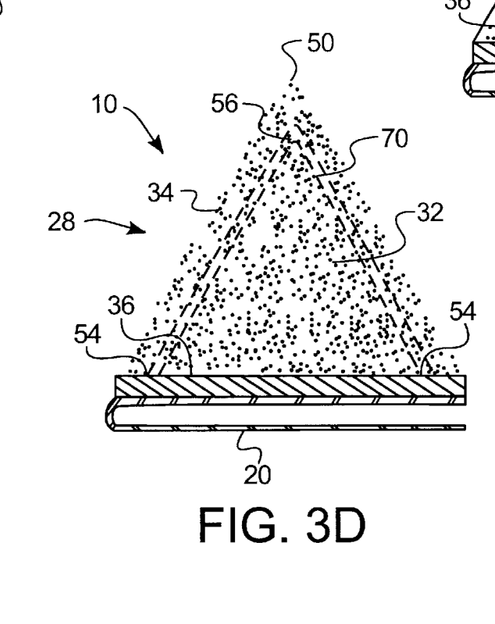
FIG. 3d shows a support wire arch replacing the abutment. There is no containment.

Refer to FIG. 3d. This design is similar to FIG. 3c except that the matrix 52 consists of wires 70 which replace the abutments. The wires are fastened to the base at points 54. The wires 70 form an arch which has a highest point at apex 56. The advantages are that the filter surrounds the matrix for a better lateral control of the velocity profile as will be discussed in the operation section.

Figure 3E:
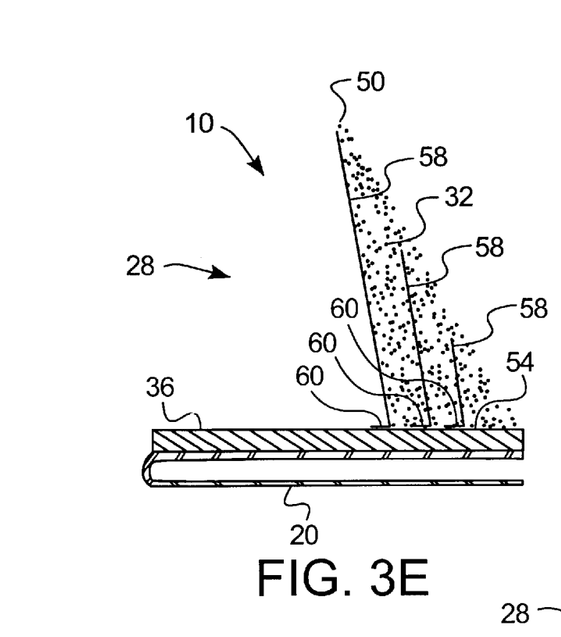
FIG. 3e shows wire screens defining the shape of the filter.

Refer to FIG. 3e. Anisotropic fibers 32 are glued to the surface of a series of screens 58 which are bent and glued to base 36 at points 60. Advantages of this construct is that the screens can be bent at will to alter the three dimensional shape of the dam 10 while operating in the field under experimental or quick adjust purposes.

Figure 3F:
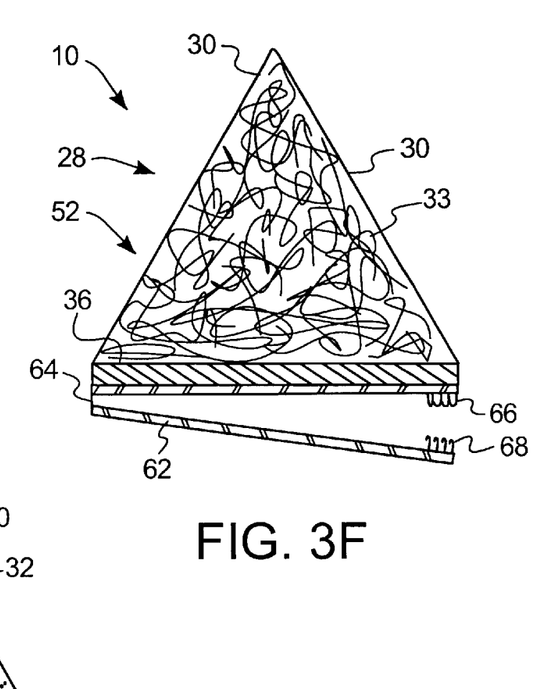
FIG. 3f shows isotropic fiber contained in the matrix and a flap type fastener under the base.

Refer to FIG. 3f. This variation addresses the problem of product liability. The methods of attachment by clip 20 can be altered to a foam rubber flap 62. A fabric hinge 64 attaches flap 62 to the edge 40 of base 36. A Velcro loop strip 66 and a Velcro hook strip 68 are attached to the opening edges of base 36 and flap 62 respectively. This arrangement allows easy fastening to strap 16 of the helmet and all materials are flexible to prevent injury in case of a crash.

Figure 3G:
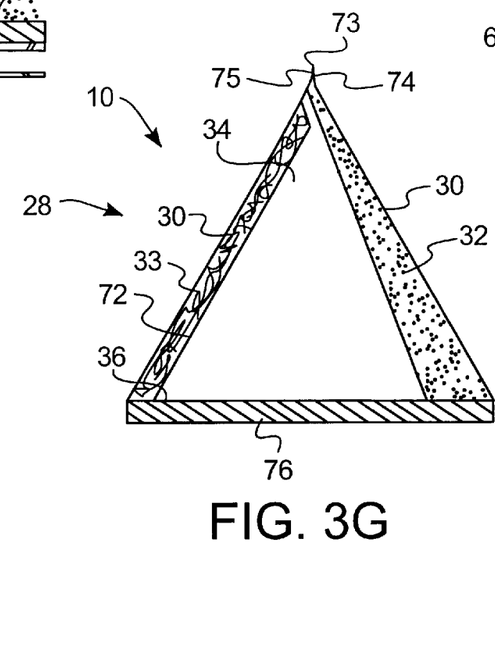
FIG. 3g shows isotropic fiber fastened to the leading edge of the abutments, a pleated tip and a base for gluing or sewing.

Refer to FIG. 3g. This variation proposes a quiet matrix and tip edge combination. The same construction of filter 32 is used as in FIG. 3a. However, the front edge 38 of abutment 34 is cut back to edge 72 to accomodate a thin strip of isotropic fibers 33 in order to act as a buffering leading edge on the abutment 34. This prevents the leading edge from whistling at high incident speeds. The containment 30 is lightly glued to the outer surface of fibers 33. Included in this design is a tip 73 which is formed by doubling back or pleating the containment netting 30 and lightly gluing the rear fold 74 of tip 73 to the front fold 75. This construct orients the tip of the containment 73 to be perpendicular to the overflow 90 at the tip 50 of the filter 32. This minimizes the flow impedance at the tip. Another feature of FIG. 3g is that the bottom of the base 36 has no clip or hinge flap, but instead relies on a contact cement 76 to adhere the aerodam to a pre-existing surface such as the dome of a helmet, or to any surface that requires turbulence control.

Figure 4:
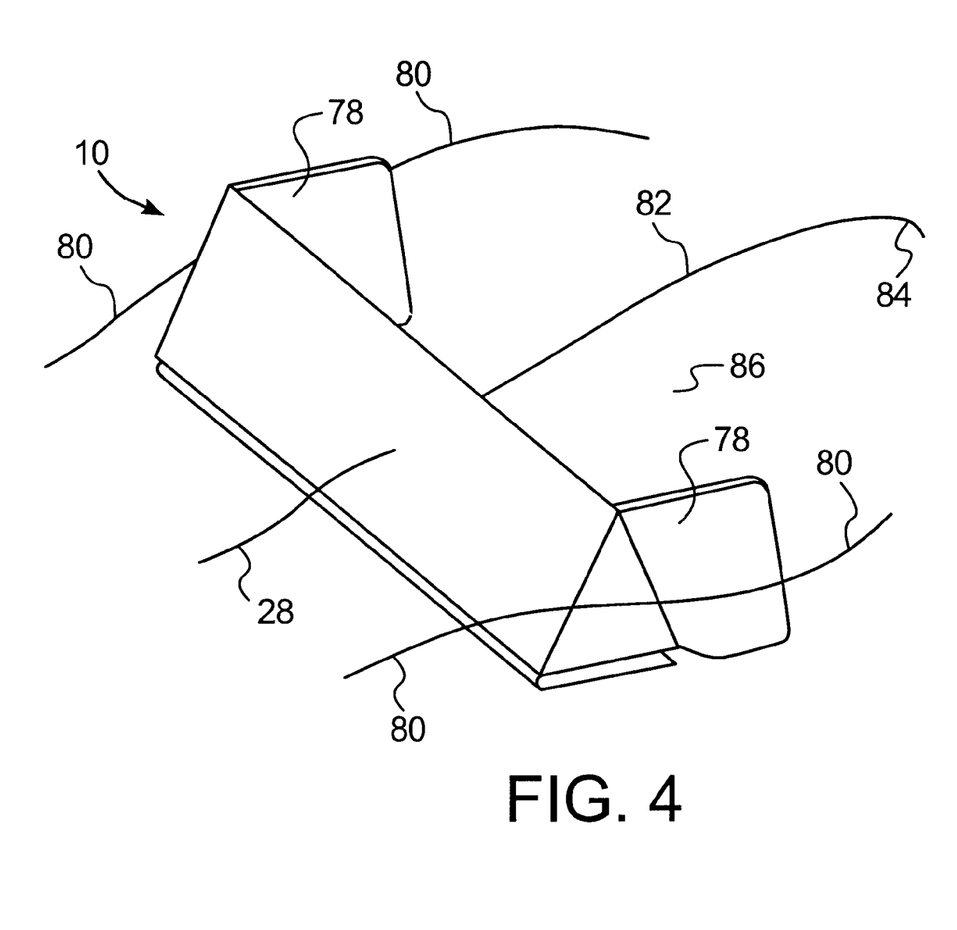
FIG. 4 shows endplates and flow lines through and around the aerodam.

Refer to FIG. 4. End plates 78 composed of foam sheeting are cemented to the rear edge 44 of the outer abutments 34. The end plates delay the end flow or wake 80 from encroaching inward toward the ear canal 14. End plates reduce the three dimensional effects on the wake 82 which is caused by the limited span of the dam. End plates also reduce the end-flow 80 when the rider's head is tilted too far up or down.

Operation

There are three regions in and around the aerodam which are responsible for the stable flow in an otherwise turbulent environment. The first is a pressure zone in front of the dam, the second is the molar viscosity within the fiber filter and the third is the laminar wake and its maintainance behind the dam and around the ear canal. The three zones will be discussed in order.

Figure 5:
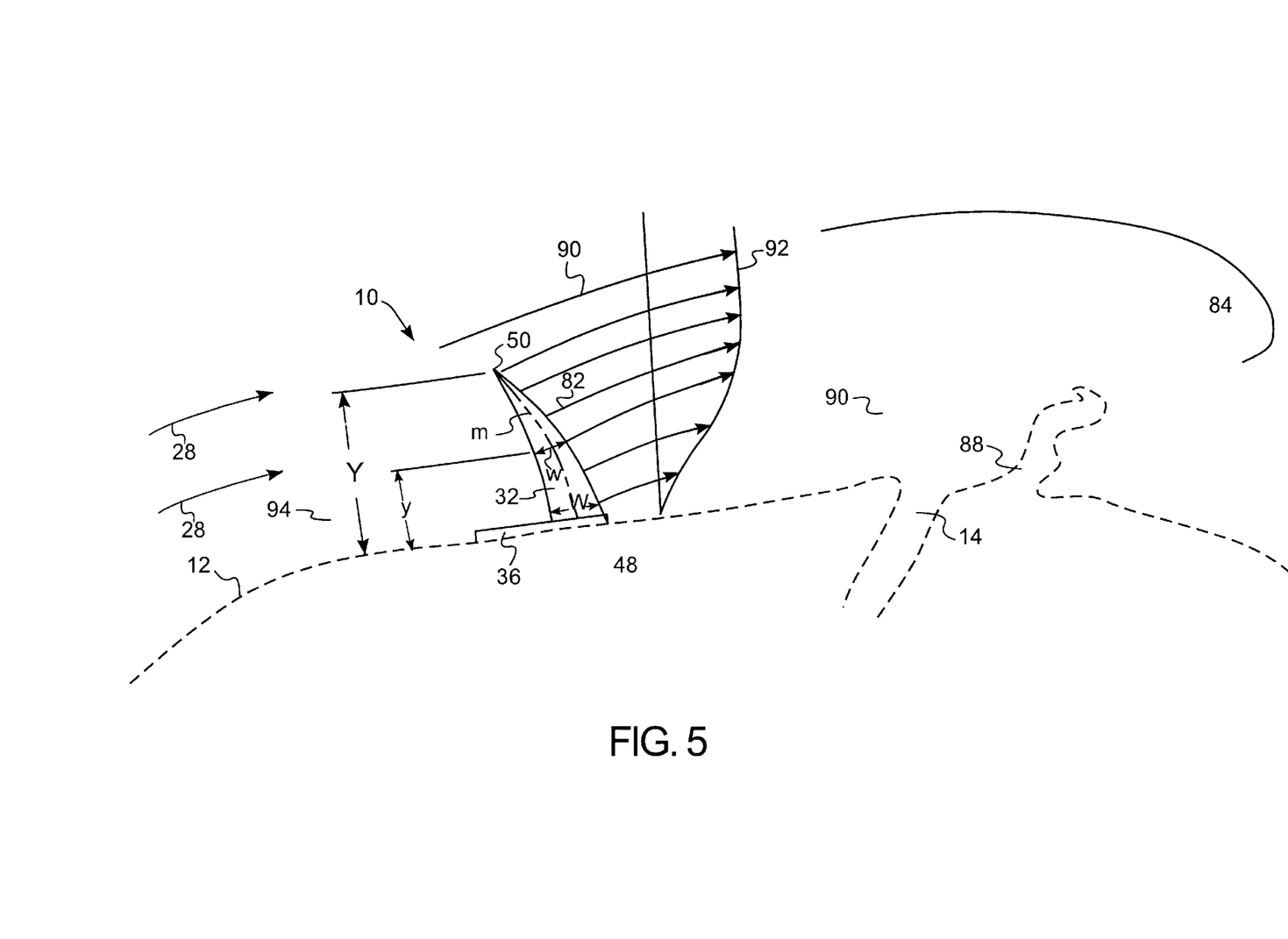
FIG. 5 is a sectional view of FIG. 1 including flow lines and pressure zones.

Refer to FIG. 5. The schematic diagram shows the fiber filter 32 having a median line m which is forward leaning. The forward leaning area between the filter 32 and the base 36 is occupied by a high pressure zone 94 just aft the cheekbone area 12 and up to a height y from the wearer's temple area. The high pressure is caused by the filter impedance. A circulation or bubble with an axis parallel to the width of the dam and perpendicular to the incoming air flow 28 is trapped in front of the filter and is stationary. Without the filter, the bubble would turn with its axis parallel to the flow 28 and induce turbulence around the temple area (Kristiansen, et.al., FIG. 6). The high pressure zone 94 stabilizes the headwind 28 so that induced turbulence is prevented. The consequence of forward stabilization is that the aerodam wake must also be stabilized. Thus, the kinetic energy developed in the pre flow will be partially consumed in pressurizing flow through the flow impedance or filter 32.

The flow through the dam must be silent if it is going to be successfully used as an aeroacoustic filter on a bicycle helmet. For this, the gauge of the fiber for filter 32 must be properly sized. If the fiber is relatively large in diameter an unstable wake will occur which can create a whistling sound called Streuhall radiation, which will have a lowest frequency of f=sv/d, where v is the speed of the air flowing around the fiber, d is either the diameter of the fiber or the distance between fibers, whichever is larger, and s is a constant. To prevent instability the diameter d must be made as small as possible so that the damping viscosity becomes the dominant force surrounding the fiber. Indeed, Taylor found that the amount of time t it takes to damp a vortex generated behind a small fiber of diameter d to one Nth its original vorticity strength is $\pi d^2/8\nu\ (N^{2/3}-1)$, where ν is the kinematic viscosity which for air is 0.14 $cm^2$/sec-(Dryden, et.al, Chapter 3.4). For a fiber diameter of 0.0025 cm (0.001 inch) and N=10, the decay time is 64 microseconds. If the flow speed past the fiber is 48.4 km/hr (30 mph) then the 1/10th decay distance is 0.86 mm (0.034 inch), which is well within the separation between the helmet strap 16 and the ear canal 14. The fiber dimensions of the type 203 or 605 STTC are ideally suited for the application of the Taylor damping function. Generally, the fiber density k to be used at the tip 50 of the filter is too dense and must be lofted to 1% or 2% fiber density by the use of a small vacuum or mechanical plucking process.

Refer again to FIG. 5. The cross section of the filter 32 comprising type 203 STTC fibers is tapered to form a wedge having a width w at a height y above the base 48 of the filter. The wedge provides a low impedance gradient or wake stabilizer where the fast overflow 90 around the wedge is prevented from breaking into turbulence by a slightly slower injection or effusion velocity 82 just below it within the height of tip 50. That injection is stabilized by yet a lower and slower velocity, etc. all the way to the base in a continuous diminuation of injection speeds so that the injection process defines the velocity profile 92.

Roll-up 84 is formed downstream and is caused by wake circulation. Like a rotating wheel, the fast overflow passes and rolls down over the slower effusion wake, in a slow, low shear stress laminar flow. When the overflow meets the surface the shear stress is suddenly increased and preturbulence may again commence. Between this point and the wedge 32 is called the null zone 86, because the flow is so quiet near the surface.

Calculations were done which fit well with field trials, such as roll-up distance as a function of Y, fiber distribution, and height as a function of camber line m. The distance from the wedge to the beginning of roll-up was observed to be about four inches behind the aerodam for one of the designs of FIG. 3.

Noise attenuation was observed to be 20 to 30 decibels in still air using the type of test described in U.S. Pat. No. 5086789 (Tichy). The noise attenuation was so complete that in a road bike test at 30 miles per hour, it was difficult to assess the accuracy of decibel drop due to the noise of the bicycle wheels on the pavement. So slight was the head wind noise that I could hear a car door shut, a small dog bark, a bird sing, and some children playing in a yard as I coasted downhill. Without turbulence abatement none of those sounds could have been heard.

The aerodam is considerably successful with many types of wedge designs. But in windy conditions where there is turbulence, soft pulsing may be felt in some designs because of the induced variations in the roll-up distance or by variations in the overflow envelope induced by Bernoulli fluctuations of the overflow. This is a universal problem for sound sensitive devices such as submarine hydrophones travelling through a turbulent sea (Strasberg), or microphones in windy conditions. The parameters mentioned above can be adjusted to minimize these non acoustic effects. In addition end plates can be quite effective at stabilizing pulses.

See FIG. 4. End plates reduce the three dimensional effects of flow by increasing the length of the injection wake 82 before roll-up 84 where stationary circulation commences, FIG. 5. The effect of end plates is to extend the null zone 86 rearward to help isolate the ear canal from the overflow 90.

Applicability and Advantages

The present invention is useful in reducing turbulence caused noise past a sound sensitive device or system without physically covering the system. By now it should be evident to one skilled in the art that the permeable aerodam concept achieves a stable injection velocity profile at any flow speed over a sound sensitive system without having to physically cover the system. The advantages over the deflection art include the lack of fabric noise over the system; an optically visible system which satisfies style requirements or optical monitoring or ventilation; easy access to the system; simplicity; ease of operation; and flexibility in design.

Uses in air include hearing protection, hearing aid protection, architectural gust abatement, automotive flow control, and drag control.

Filter methods can be redesigned to render use in any fluid medium other than air, such as water, blood or explosive liquids and gasses where flow separation at a critical point may be prevented.

The methods of base mounting are not limited to those mentioned in the embodiments, but can cover welded, bolted, sewn, glued, or magnetic strip attachments as well.

Methods of filter support may cover integrated matrix and filter or a discrete matrix labyrinth with filter.

Although the present invention is useful in the control of fluid flow, many other varied embodiments that incorporate the teachings of the present invention may be easily constructed by those skilled in the art.

SUMMARY

High speed flow separates from a convex surface which ultimately causes turbulence downstream. To calm the flow an aerodam comprising a tilt-up filter is strategically placed so that the flow impedance of the filter causes a forward pressure zone at the point of separation. The filter impedes the near-surface flow by an in-situ process, causing a design shaped wake velocity profile. The profile wake injects stabilized flow beneath the overflow so that a local laminar flow regime is created. A null zone is created downstream providing a quiet flow environment. Ambient sounds are simply not affected. Since the aerodam is forward positioned, the null zone falls in the same position as the ear canal. The null zone is also a good place to put a microphone or a hydrophone for underwater use. The success of the filter depends on its tilt angle, fiber density, fiber diameter and the height of the aerodam.

REFERENCES

D. Smith, March 1993 Bicycling, "Questions and Answers, Wind Noise", pp 43–44.

U. R. Kristiansen, O. K. Pettersen, 1978 Journal of Sound and Vibration, "Experiments on the Noise Heard by Human Beings When Exposed to Atmospheric Winds", 58(2),285–291.

W. K. Van Moorheim, et.al., 1981 Journal of Sound and Vibration, "The Effects of Motorcycle Helmets on Hearing and the Detection of Learning Signals", 77(1),39–49.

Hugh L. Dryden, et.al., 1956 Hydrodynamics, Dover Publications, Inc., New York, Chapter 3.4 "The Growth and Decay of Vortex Motion", pp212–222.

Jacob Bear, 1972 Dynamics of Fluids in Porous Media, Dover Publications, Inc., New York.

M. Strasberg, 1979 J. Acoust. Soc. Am., "Nonacoustic Noise Interference on Measurements of Infrasonic Ambient Noise", 65(5)Nov. pp 1487–1493.

What is claimed is:

1. A wind noise reducing, partially permeable aerodynamic dam to be worn on a front helmet strap of a wearer's helmet assembly, the dam comprising:

a base having a width parallel to said strap, a length perpendicular to said strap, an inner surface defined by said length and width, said surface having attachable means attached to said strap, the base having an outer surface;

a matrix attached to said outer surface, the matrix having a height which is normal to said outer surface of base, the matrix having sufficient stiffness to support against wind pressure, the matrix also comprising a design shaped permeable structure;

a group of filaments which are supported and attached to said matrix to at least within the confines of said matrix, the attached fiber forming a design shaped filter having at least said height and width, the filter having a thickness in the direction of said length, said thickness shaped according to a predetermined design;

whereby said filter causes a tortuous path impedance to an incoming wind generally parallel to said length, resulting in a three dimensional flow velocity profile which provides a quiet retrolaminar wake past the wearer's ear canal.

2. An apparatus of claim 1 wherein matrix is covered by an enclosure comprising a netting.

3. An apparatus of claim 1 wherein the matrix comprises a plurality of arches, the legs of the arches attached to said base, and where the apeces of the arches define an arc over said base.

4. An apparatus of claim 1 wherein the matrix is comprised of a plurality of supportive fibers attached to in the base.

5. An apparatus of claim 1 wherein the matrix is comprised of an array of spaced apart tab-like abutments, the plane of all tabs being parallel to said incoming air flow and perpendicular to the base.

6. An apparatus of claim 5 wherein the outboard abutments extend aft the said filter to form end plates.

7. An apparatus of claim 5 wherein filament ends are fused to adjacent abutment surfaces.

8. An apparatus of claim 1 wherein the matrix comprises one or more flow permeable screens.

9. An apparatus of claim 1 wherein said base inner surface includes a friction clip for fastening said dam onto said helmet strap.

10. An apparatus of claim 1 wherein the base inner surface includes a hinged flap with a hook and loop closer to wrap around and close onto said helmet strap.

11. An apparatus of claim 1 wherein said filter is covered by an enclosure comprising a netting.

12. An apparatus of claim 1 wherein said base is sewn onto said helmet strap.

13. An apparatus of claim 2 wherein said enclosure is pleated at the tip edge of said matrix.

14. An apparatus of claim 5 wherein the leading edges of said abutments are recessed and lined with fiber.

15. A porous flow barrier comprising:

a base having an outer surface and an inner surface, the inner surface having attachable means attached to a pre existing surface;

at least one screen having a weft and a warp, the weft composed of support wires, one end of each wire being fastened to said outer surface, the weft wires having sufficient stiffness to be resistant to bending, the warp composed of filaments generally parallel to said outer surface, the filaments designed to be spaced apart sufficiently to form a filter;

whereby said filter provides an impedance to flow parallel to said pre existing surface and perpendicular to said screen, said impedance having a gradient as a function of said design spacing so that a flow velocity profile is created which resists the onset of turbulence.

16. An apparatus of claim 15 wherein said separation between warp filaments becomes greater as the distance increases above said outer surface.

17. An apparatus of claim 15 wherein said attachable means of inner surface comprises a means of fastening to a strap which is held firmly against a pre existing surface.

18. An apparatus of claim 15 wherein each said screen defines a compound surface.

* * * * *